(12) United States Patent
Meister et al.

(10) Patent No.: US 9,393,413 B2
(45) Date of Patent: Jul. 19, 2016

(54) FEEDBACK GATING OF AN ENERGY SIGNAL FOR NEURAL STIMULATION

(71) Applicant: MED-EL Elektromedizinische Geraete GmbH, Innsbruck (AT)

(72) Inventors: Dirk Meister, Innsbruck (AT); Peter Schleich, Telfs (AT); Thomas Schwarzenbeck, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

(21) Appl. No.: 14/565,504

(22) Filed: Dec. 10, 2014

(65) Prior Publication Data

US 2015/0163605 A1    Jun. 11, 2015

Related U.S. Application Data

(60) Provisional application No. 61/914,515, filed on Dec. 11, 2013.

(51) Int. Cl.
   *A61N 1/00* (2006.01)
   *A61N 1/36* (2006.01)
   *A61N 1/05* (2006.01)

(52) U.S. Cl.
   CPC ........... *A61N 1/36032* (2013.01); *A61N 1/0541* (2013.01)

(58) Field of Classification Search
   CPC ................. A61N 1/36032; A61N 1/0541
   USPC ........................................................ 607/57
   See application file for complete search history.

(56) References Cited

U.S. PATENT DOCUMENTS

| | | | |
|---|---|---|---|
| 7,171,272 B2 | 1/2007 | Blamey et al. | 607/57 |
| 2005/0171579 A1* | 8/2005 | Tasche | A61N 1/0551 607/57 |
| 2006/0227986 A1* | 10/2006 | Swanson | H04R 25/606 381/312 |
| 2011/0066210 A1* | 3/2011 | Wilson | A61N 1/36032 607/57 |
| 2011/0098784 A1 | 4/2011 | Schleich et al. | 607/57 |
| 2012/0209351 A1 | 8/2012 | Meister et al. | 607/57 |
| 2013/0259167 A1 | 10/2013 | Yoon et al. | 375/340 |

OTHER PUBLICATIONS

"Psychometric functions and temporal integration in electric hearing", The Journal of Acoustical Society of America; Jun. 1997; vol. 101, Issue 6, pp. 3706-3721.*
Donaldson, et al, "Psychometric functions and temporal integration in electric hearing", *The Journal of Acoustical Society of America*, Jun. 1997; vol. 101, Issue 6, pp. 3706-3721, 16 pages.
International Searching Authority, Authorized Officer Blaine R. Copenheaver, International Search Report and Written Opinion—PCT/US2014/069434, date of mailing Feb. 23, 2015, 16 pages.

* cited by examiner

*Primary Examiner* — Amanda Patton
*Assistant Examiner* — Philip C Edwards
(74) *Attorney, Agent, or Firm* — Sunstein Kann Murphy & Timbers LLP

(57) ABSTRACT

A system and method are described for generating electrode stimulation signals for electrode contacts in a cochlear implant electrode array. An input audio signal is processed to generate band pass channel signals that each represent an associated band of audio frequencies. From each channel signal channel, audio information is extracted including a channel signal envelope reflecting channel signal energy. Initial electrode stimulation pulses are then generated based on the band pass signal envelopes. A gating function is applied to the initial electrode stimulation pulses based on a gating feedback signal characterizing preceding stimulation signals to produce gated electrode stimulation pulses. The gated electrode stimulation pulses are set to the initial electrode stimulation signals when the band pass signal envelopes are greater than the gating feedback signal, and otherwise are set to zero.

18 Claims, 6 Drawing Sheets

FEEDBACK GATING OF AN ENERGY SIGNAL FOR NEURAL STIMULATION

This application claims priority from U.S. Provisional Patent Application 61/914,515, filed Dec. 11, 2013, which is incorporated herein by reference in its entirety.

FIELD OF THE INVENTION

The present invention relates to hearing implant systems such as cochlear implants, and specifically to the signal processing used therein.

BACKGROUND ART

A normal ear transmits sounds as shown in FIG. 1 through the outer ear 101 to the tympanic membrane (eardrum) 102, which moves the bones of the middle ear 103 (malleus, incus, and stapes) that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, auditory prostheses have been developed. For example, when the impairment is related to operation of the middle ear 103, a conventional hearing aid may be used to provide acoustic-mechanical stimulation to the auditory system in the form of amplified sound. Or when the impairment is associated with the cochlea 104, a cochlear implant (CI) with an implanted stimulation electrode can electrically stimulate auditory nerve tissue with small currents delivered by multiple electrode contacts distributed along the electrode.

FIG. 1 also shows some components of a typical cochlear implant system which includes an external microphone that provides an audio signal input to an external signal processor 111 where various signal processing schemes can be implemented. The processed signal is then converted into a digital data format, such as a sequence of data frames, for transmission into the implant 108. Besides receiving the processed audio information, the implant 108 also performs additional signal processing such as error correction, pulse formation, etc., and produces a stimulation pattern (based on the extracted audio information) that is sent through an electrode lead 109 to an implanted electrode array 110.

Typically, the electrode array 110 includes multiple electrode contacts 112 on its surface that provide selective stimulation of the cochlea 104. Various signal processing schemes can be implemented to produce the electrical stimulation signals applied by the electrode contacts 112. Most of these represent split an incoming sound signal into distinct frequency bands and extract the energy envelope of each band. These envelope representations of the sound signal are used to define the pulse amplitude of stimulation pulses to each electrode contact 112. The number of band pass signals typically equals the number of electrode contacts 112, and relatively broad frequency bands are needed to cover the acoustic frequency range. Each electrode contact 112 delivers electric stimulation signals to its adjacent neural tissue for a defined frequency band reflecting the tonotopic organization of the cochlea 104.

Signal processing approaches that are well-known in the field of cochlear implants include continuous interleaved sampling (CIS) digital signal processing, channel specific sampling sequences (CSSS) digital signal processing (as described in U.S. Pat. No. 6,348,070, incorporated herein by reference), spectral peak (SPEAK) digital signal processing, and compressed analog (CA) signal processing. For example, in the CIS approach, signal processing for the speech processor involves the following steps:

(1) splitting up of the audio frequency range into spectral bands by means of a filter bank,
(2) envelope detection of each filter output signal,
(3) instantaneous nonlinear compression of the envelope signal (map law).

According to the tonotopic organization of the cochlea, each stimulation electrode in the scala tympani is associated with a band pass filter of the external filter bank. For stimulation, symmetrical biphasic current pulses are applied. The amplitudes of the stimulation pulses are directly obtained from the compressed envelope signals. These signals are sampled sequentially, and the stimulation pulses are applied in a strictly non-overlapping sequence. Thus, as a typical CIS-feature, only one stimulation channel is active at one time and the overall stimulation rate is comparatively high.

For example, assuming an overall stimulation rate of 18 kpps and a 12 channel filter bank, the stimulation rate per channel is 1.5 kpps. Such a stimulation rate per channel usually is sufficient for adequate temporal representation of the envelope signal. The maximum overall stimulation rate is limited by the minimum phase duration per pulse. The phase duration cannot be chosen arbitrarily short, because the shorter the pulses, the higher the current amplitudes have to be to elicit action potentials in neurons, and current amplitudes are limited for various practical reasons. For an overall stimulation rate of 18 kpps, the phase duration is 27 μs, which is near the lower limit. Each output of the CIS band pass filters can roughly be regarded as a sinusoid at the center frequency of the band pass filter which is modulated by the envelope signal. This is due to the quality factor ($Q \approx 3$) of the filters. In case of a voiced speech segment, this envelope is approximately periodic, and the repetition rate is equal to the pitch frequency.

In the existing CIS-strategy, only the envelope signals are used for further processing, i.e., they contain the entire stimulation information. For each channel, the envelope is represented as a sequence of biphasic pulses at a constant repetition rate. A characteristic feature of CIS is that this repetition rate (typically 1.5 kpps) is equal for all channels and there is no relation to the center frequencies of the individual channels. It is intended that the repetition rate is not a temporal cue for the patient, i.e., it should be sufficiently high, so that the patient does not perceive tones with a frequency equal to the repetition rate. The repetition rate is usually chosen at greater than twice the bandwidth of the envelope signals (Nyquist theorem).

Another cochlear implant stimulation strategy that transmits fine time structure information is the Fine Structure Processing (FSP) strategy by Med-El. Zero crossings of the band pass filtered time signals are tracked, and at each negative to positive zero crossing a Channel Specific Sampling Sequence (CSSS) is started. Typically CSSS sequences are only applied on the first one or two most apical channels, covering the frequency range up to 200 or 330 Hz. The FSP arrangement is described further in Hochmair I, Nopp P, Jolly C, Schmidt M, Schößer H, Garnham C, Anderson I, *MED-EL Cochlear Implants: State of the Art and a Glimpse into the Future*, Trends in Amplification, vol. 10, 201-219, 2006, which is incorporated herein by reference.

FIG. 2 shows major functional blocks in the signal processing arrangement typical of existing cochlear implant (CI) systems wherein band pass signals containing stimulation timing and amplitude information are assigned to stimulation electrodes. Preprocessor Filter Bank 201 pre-processes an initial acoustic audio signal, e.g., automatic gain control, noise reduction, etc. Each band pass filter in the Preprocessor Filter Bank 201 is associated with a specific band of audio frequencies so that the acoustic audio signal is filtered into some N band pass signals, $B_1$ to $B_N$ where each signal corresponds to the band of frequencies for one of the band pass filters.

The band pass signals $B_1$ to $B_N$ (which can also be thought of as frequency channels) are input to a Stimulation Pulse Generator 202 which extracts signal specific stimulation information—e.g., envelope information, phase information, timing of requested stimulation events, etc.—into a set of N stimulation event signals $S_1$ to $S_N$, which represent electrode specific requested stimulation events. For example, channel specific sampling sequences (CSSS) may be used as described in U.S. Pat. No. 6,594,525, which is incorporated herein by reference.

Pulse Mapping Module 203 applies a non-linear mapping function (typically logarithmic) to the amplitude of each band-pass envelope. This mapping function typically is adapted to the needs of the individual CI user during fitting of the implant in order to achieve natural loudness growth. This may be in the specific form of functions that are applied to each requested stimulation event signal $S_1$ to $S_N$ that reflect patient-specific perceptual characteristics to produce a set of electrode stimulation signals $A_1$ to $A_M$ that provide an optimal electric representation of the acoustic signal.

The Pulse Mapping Module 203 controls loudness mapping functions. The amplitudes of the electrical pulses are derived from the envelopes of the assigned band pass filter outputs. A logarithmic function with a form-factor C typically may be applied to stimulation event signals $S_1$ to $S_N$ as a loudness mapping function, which typically is identical across all the band pass analysis channels. In different systems, different specific loudness mapping functions other than a logarithmic function may be used, with just one identical function is applied to all channels or one individual function for each channel to produce the electrode stimulation signals $A_1$ to $A_M$ outputs from the Pulse Mapping Module 203.

Patient specific stimulation is achieved by individual amplitude mapping and pulse shape definition in Pulse Shaper 204 which develops the set of electrode stimulation signals $A_1$ to $A_M$ into a set of output electrode pulses $E_1$ to $E_M$ to the electrodes in the implanted electrode array which stimulate the adjacent nerve tissue.

The response of a neuron to an electrical stimulus depends on its previous stimulation history. This behavior has been termed adaption, which can temporally range from milliseconds (short term adaption) up to seconds (long-term adaption). See Zilany et al., *A Phenomenological Model of the Synapse Between the Inner Hair Cell and Auditory Nerve: Long-Term Adaptation with Power-Law Dynamics*, J Acoust Soc Am.; November 2009; 126(5):2390-412, which is incorporated herein by reference in its entirety. Adaption may result in so-called refractory periods during which an applied stimulus will not evoke a response from the neuron.

In the multichannel stimulation of a cochlear implant system, the electrical field of applied stimulation pulses spreads over a relatively wide area in the cochlea and thus generates an undesired smearing of the transmitted information, i.e. a bundle of undesired neighbouring nerve fibres may be excited or elicited. This is referred to as channel crosstalk. Pulses that are applied during the refractory period of a nerve fiber transmit little or no information and may, through channel crosstalk, generate unwanted stimulation at neural sites that are not intended to be stimulated.

Traditional CI processing schemes such as CIS do not take into account any adaption processes. Thus, a large amount of the stimulation pulses of these strategies may result in channel crosstalk stimulation. Various different approaches have focused on "sparse" stimulation for cochlear implants and have tried to identify those times when stimulation would be most effective. Sit et al., *A Low-Power Asynchronous Interleaved Sampling Algorithm for Cochlear Implants that Encodes Envelope and Phase Information*, IEEE Trans Biomed Eng.; January 2007; 54(1):138-49 (which is incorporated herein by reference in its entirety) describes an approach referred to as asynchronous interleaved sampling (AIS) that charges a capacitor with the incoming signal until spikes are generated and thereby makes use of a longer term behavior of the incoming signal. U.S. Patent Publication 20090125082 (which is incorporated herein by reference in its entirety) describes an approach known as Pulsatile Implant Stimulation (PIS) that uses a refractory period to avoid stimulation directly after a pulse was applied but only the previous pulse is considered. Li et al., *Sparse Stimuli for Cochlear Implants*, EUSIPCO, Lausanne, Switzerland, Aug. 25-29, 2008 (which is incorporated herein by reference in its entirety) describes a sparse coding approach that selects essential speech information out of a noisy speech input signal for simulating auditory neurons and thereby reduces interaction between channels.

SUMMARY OF THE INVENTION

Embodiments of the present invention are directed to methods, systems and software code for generating electrode stimulation signals for electrode contacts in a cochlear implant electrode array. An input audio signal is processed to generate band pass channel signals that each represent an associated band of audio frequencies. From each channel signal channel, audio information is extracted including a channel signal envelope reflecting channel signal energy. Initial electrode stimulation pulses are then generated based on the band pass signal envelopes. A gating function is applied to the initial electrode stimulation pulses based on a gating feedback signal characterizing preceding stimulation signals to produce gated electrode stimulation pulses. The gated electrode stimulation pulses are set to the initial electrode stimulation signals when the band pass signal envelopes are greater than the gating feedback signal, and otherwise are set to zero. Output stimulation pulses are provided to the electrode contacts based on the gated electrode stimulation pulses, and the gating feedback signal is produced from the output stimulation pulses for the gating function.

The gating function may specifically be a leaky integrator gating function or a low pass filter gating function. The gating function may reflect a mathematical model of stimulated tissue ion concentration and/or neurotransmitters in inner hair cells. The gating function may reflect a frequency dependent weighting constant and/or channel crosstalk between adjacent frequency channels. The stimulation pulses may be produced based on a continuous interleaved sampling (CIS) approach or a fine structure processing (FSP) approach.

DETAILED DESCRIPTION OF SPECIFIC EMBODIMENTS

Embodiments of the present invention stimulate auditory neurons in a more effective way that also reduces the effects of channel crosstalk by manipulating the energy function (signal envelope) used for stimulation and taking into account past stimulation events by gating an energy feedback signal.

Figure 1:
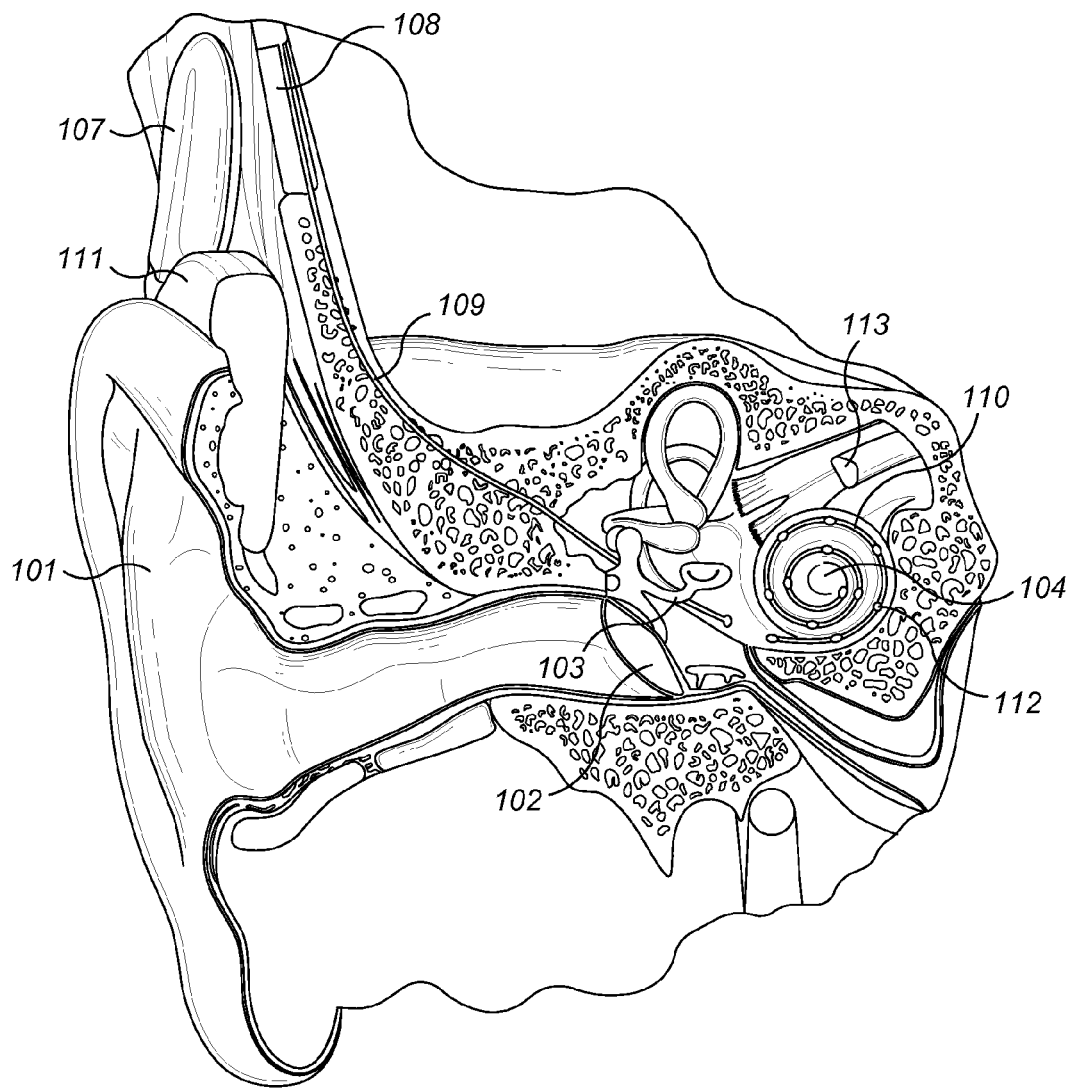
FIG. 1 shows the anatomy of a typical human ear and components in a cochlear implant system.
Figure 2:
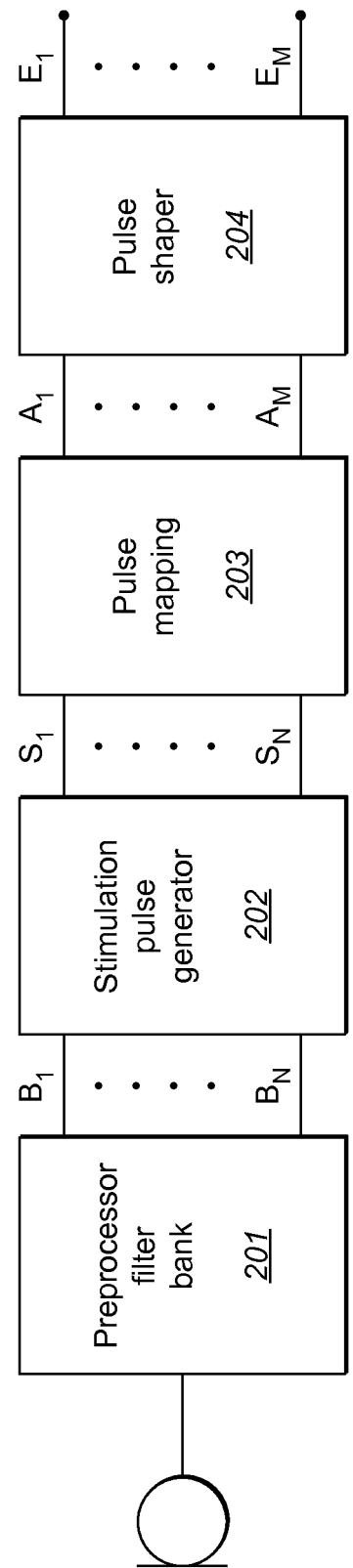
FIG. 2 shows major signal processing blocks of a typical cochlear implant system.
Figure 3:
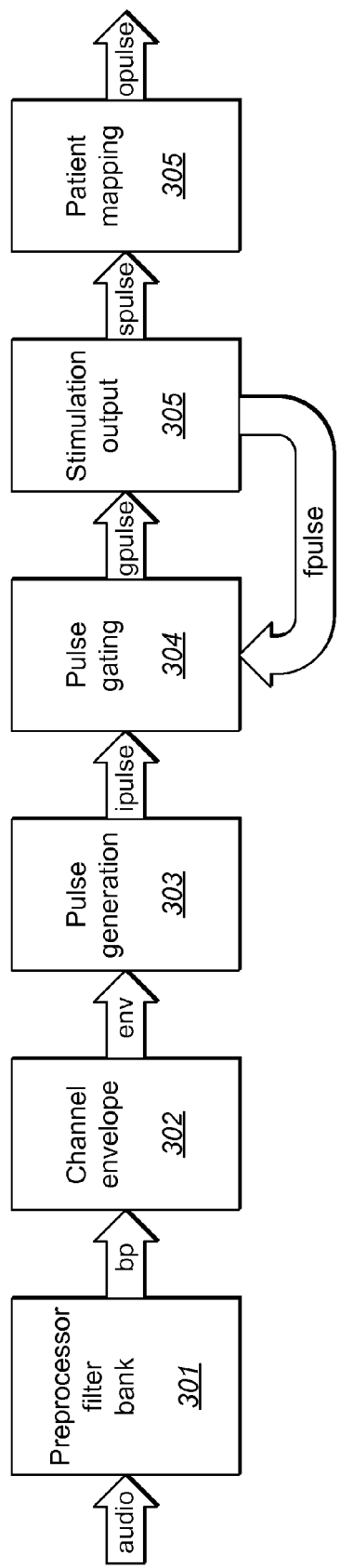
FIG. 3 shows a functional block diagram of CI signal processing with energy signal feedback gating according to an embodiment of the present invention.

FIG. 3 shows a functional block diagram of CI signal processing with energy signal feedback gating according to an embodiment of the present invention. Pre-processor filter bank 301 processes an input audio signal audio to generate band pass channel signals bp that each represent an associated band of audio frequencies. Depending on context, the band pass channel signals bp can also be thought of as the frequency channels.

Channel envelope module 302 then extracts from each band pass channel signal bp audio information that includes a channel signal envelope env reflecting channel signal energy. Other audio information that may be extracted by the channel envelope module 302 may include signals such as the fine time structure (carrier or zero crossings) of the band pass channel signals bp.

Pulse generation module 303 then generates initial electrode stimulation pulses ipulse based on the band pass signal envelopes env from the channel envelope module 302. For example, the pulse generation module 303 may sample the channel signal envelope env in a regular time grid as it is done with CIS processing, or by scaling channel-specific sampling sequences with the envelope as in FSP processing (e.g., as in U.S. Patent Publication 2011/0230934).

Pulse gating module 304 gates the electrode stimulation pulses by applying a gating function fg to the initial electrode stimulation pulses ipulse based on a gating feedback signal fpulse that characterizes preceding stimulation signals. At a sampling point n in time, the pulse gating module 304 sets the stimulation pulses gpulse to the initial stimulation pulses ipulse when the band pass signal envelopes env are greater than the gating feedback signal fpulse. Otherwise the pulse gating module 304 sets the stimulation pulses gpulse to zero. In pseudocode, the calculation at sampling point n in time of the gated pulse signal gpulse(n) in the pulse gating module 304 can be described as:

if $(fg(n)*w) > env(n)$ gpulse($n$)=0;

else gpulse($n$)=ipulse($n$);

where w is a band specific weighting factor or function.

The gating function fg specifically can be a leaky integrator. When n denotes sampling points in time and k is a constant factor that is smaller than one, then a simple realization of a leaky integrator of the stimulation pulses spulse is:

$$fg(n) = k*fg(n-1) + spulses(n) \quad (1)$$

In other embodiments, the gating function fg may specifically be based on a low pass filter, a mathematical model of ion concentrations of the stimulated nerve, or a model of neurotransmitter concentrations of the Inner Hair Cells (IHCs). In some embodiments the integration constant k may be frequency (channel)-dependent.

Stimulation output module 305 then provides stimulation frame pulses spulse based on the gated electrode stimulation pulses gpulse; for example, by CIS or by n-of-m type stimulation strategies. The stimulation output module 305 also produces the gating feedback signal fpulse from the stimulation frame pulses spulse for the gating function fg in the pulse gating module 304.

Mapping module 306 scales the stimulation frame pulses spulse by patient-specific fitting parameters to produce the final output stimulation pulses opulse that account for individual charge requirements and dynamic ranges. In some embodiments, the mapping module 306 may produce the gating feedback signal fpulse rather than the stimulation output module 305.

Figure 4:
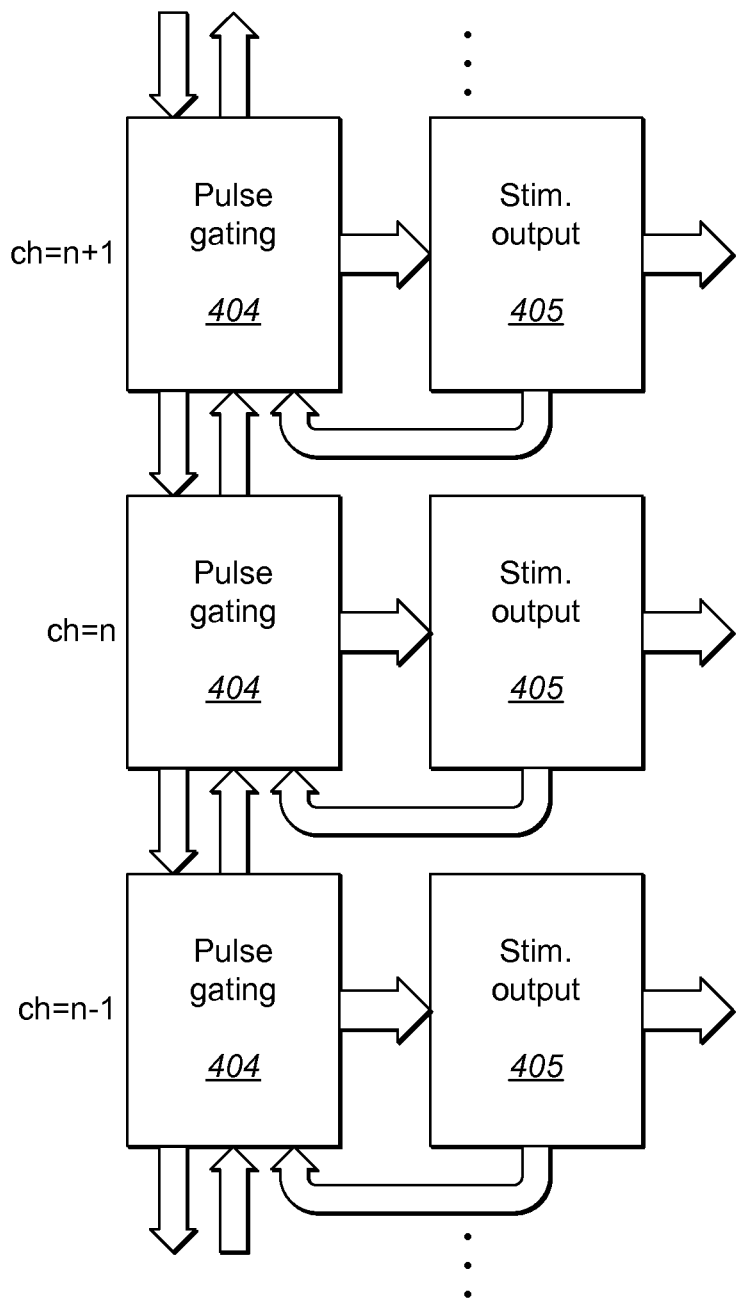
FIG. 4 shows a modified processing arrangement including channel crosstalk according to an embodiment of the present invention.

FIG. 4 shows a modified processing arrangement including channel crosstalk according to an embodiment of the present invention by combining the gating function of adjacent channels. If ch denotes the channel number (e.g. ch=1 is the lowest channel in frequency, ch=12 is the highest channel in frequency), then a gating function fgCross that considers channel crosstalk could be computed by the pulse gating module 404 as:

$$fg\text{Cross}_{ch}(n) = \alpha * fg_{ch-1}(n) + fg_{ch}(n) + \beta * fg_{ch+1}(n)$$

where $\alpha$ and $\beta$ are factors smaller than one that resemble the decrease of the electrical field towards apical and basal directions respectively. The pulse gating would then be performed with fgCross:

if $(fg\text{Cross}(n)*w) > env(n)$ gpulses($n$)=0;

else gpulses($n$)=pulses($n$).

Figure 5:
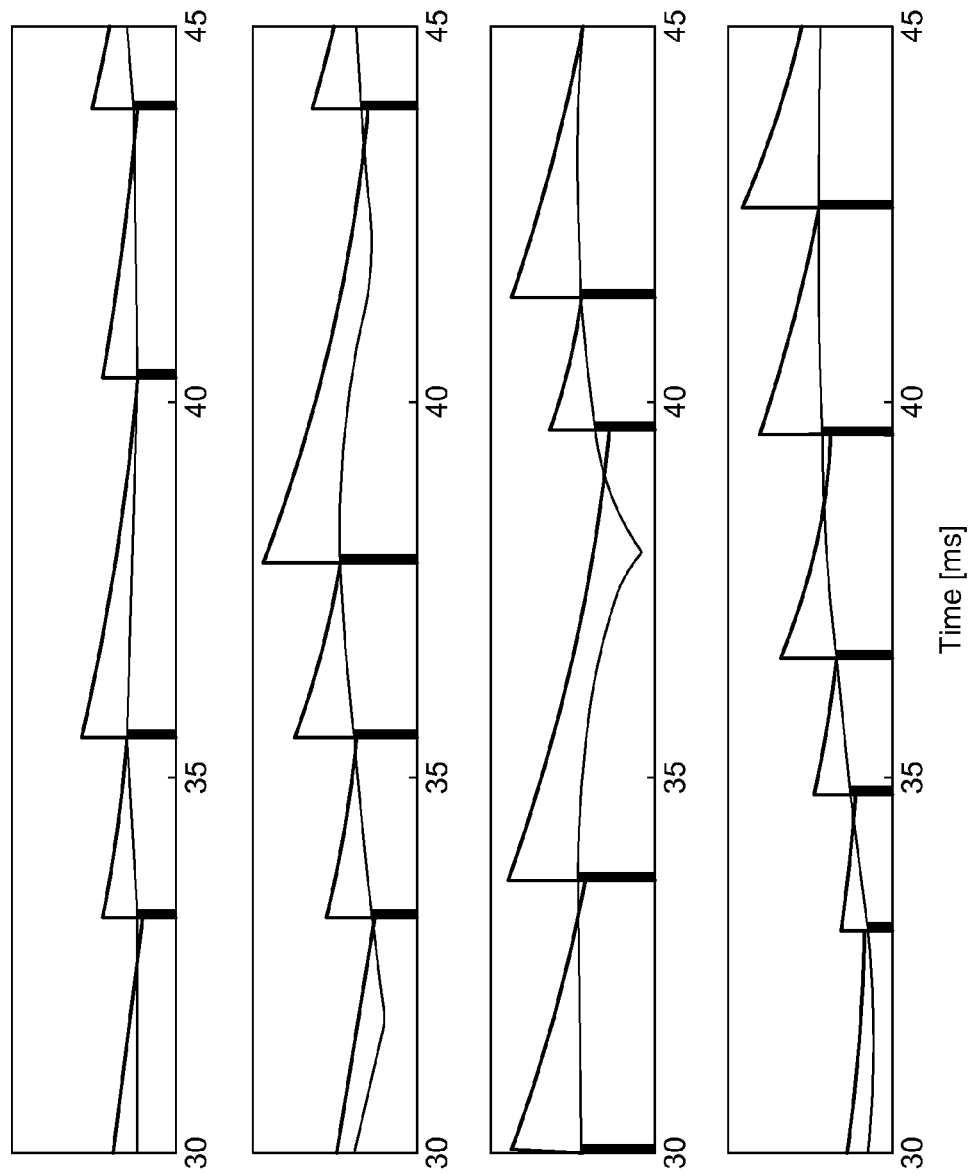
FIG. 5 shows an example graph of signal gating according to an embodiment of the present invention with a leaky integrator gating function.

FIG. 5 shows an example graph of signal gating according to an embodiment of the present invention with a leaky integrator gating function where the stimulation pulses spulse are computed with a leaky integrator. The input audio in FIG. 5 is a sample of the vowel "a" and the first four channels of a 12-channel filter bank are drawn in the graph. In this example, the time constant for the leaky integrator k is set to 0.99. The solid black line shows the gating function fg, the light grey line denotes band pass envelope signals env, and the bars represent gated stimulation pulses gpulse.

Figure 6:
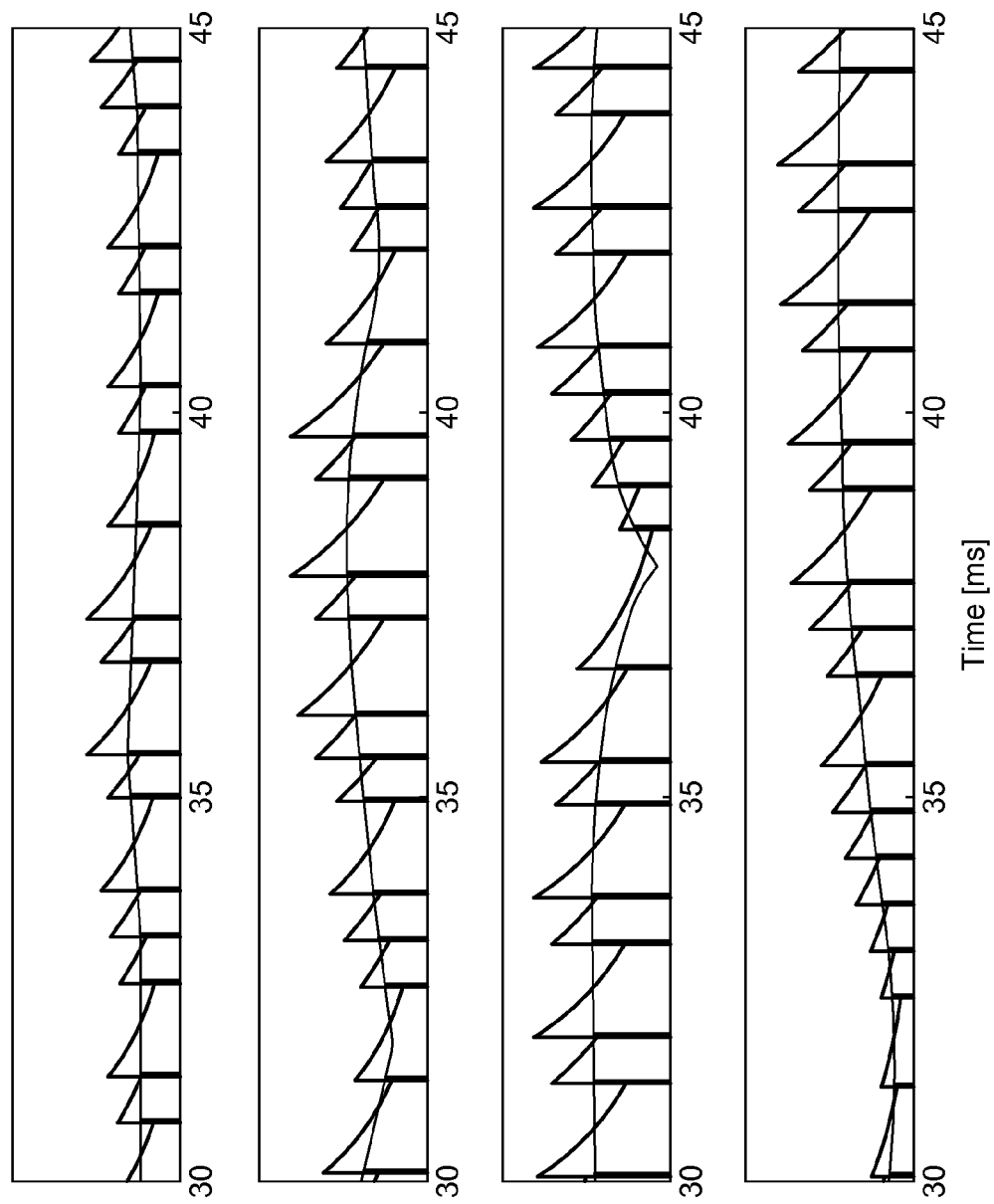
FIG. 6 shows an example graph of signal gating according to an embodiment of the present invention with a first-order low-pass filter.

FIG. 6 shows an example graph of signal gating according to an embodiment of the present invention with a first-order low-pass filter that produces the gated pulses gpulse. A similar audio input signal is used as in FIG. 5 and the cut-off frequency of the low-pass filter is set to 300 Hz. Again, the solid black line shows the gating function fg, the light grey line the band pass envelope signals env, and the bar the gated stimulation pulses gpulse.

Embodiments of the present invention as described above take into account the long term adaption of nerve fibers and so a more physiological stimulation of the neural tissue can be achieved. In addition, channel crosstalk can be minimized since stimulation rate is reduced and only essential pulses are applied. Channel crosstalk of applied pulses can be included in computation of the gating function and thereby avoid ineffective stimulation of neural regions that are in a post-stimulation refractory state from adjacent channels. Energy consumption also is reduced due to the reduced stimulation rate.

Embodiments of the invention may be implemented in part in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A method of generating electrode stimulation signals for electrode contacts in a cochlear implant electrode array, the method comprising:
    processing an input audio signal to generate a plurality of band pass channel signals each representing an associated band of audio frequencies;
    extracting from each channel signal channel audio information including a channel signal envelope reflecting channel signal energy;
    generating initial electrode stimulation pulses based on the band pass signal envelopes;
    applying a gating function to the initial electrode stimulation pulses based on a gating feedback signal characterizing preceding stimulation signals to produce gated electrode stimulation pulses, wherein the gated electrode stimulation pulses:
        i. are set to the initial electrode stimulation signals when the band pass signal envelopes are greater than the gating feedback signal, and
        ii. otherwise are set to zero;
    providing output stimulation pulses to the electrode contacts based on the gated electrode stimulation pulses; and
    producing the gating feedback signal from the output stimulation pulses for the gating function.

2. The method according to claim 1, wherein the gating function is a leaky integrator gating function.

3. The method according to claim 1, wherein the gating function is a low pass filter gating function.

4. The method of claim 1, wherein the gating function reflects a mathematical model of stimulated tissue ion concentration.

5. The method of claim 1, wherein the gating function reflects a mathematical model of neurotransmitters in inner hair cells.

6. The method of claim 1, wherein the gating function includes a frequency dependent weighting constant.

7. The method of claim 1, wherein the gating function takes into account channel crosstalk between adjacent frequency channels.

8. The method of claim 1, wherein the stimulation pulses are produced based on a continuous interleaved sampling (CIS) approach.

9. The method of claim 1, wherein the stimulation pulses are produced based on a fine structure processing (FSP) approach.

10. A signal processing system for generating electrode stimulation signals for electrode contacts in a cochlear implant electrode array, the system comprising:
    a filter bank pre-processor configured to process an input audio signal to generate a plurality of band pass channel signals each representing an associated band of audio frequencies;
    a channel envelope module coupled to the filter bank pre-processor and configured to extract from each channel signal channel audio information including a channel envelope signal reflecting channel signal energy;
    a pulse generation module coupled to the channel envelope module and configured to generate initial electrode stimulation pulses based on the band pass signal envelopes;
    a pulse gating module coupled to the pulse generation module and configured to apply a gating function to the initial electrode stimulation pulses based on a gating feedback signal characterizing preceding stimulation signals to produce gated electrode stimulation pulses, wherein the gated electrode stimulation pulses:
        i. are set to the initial electrode stimulation signals when the band pass signal envelopes are greater than the gating feedback signal, and
        ii. otherwise are set to zero; and
    a stimulation output module coupled to the pulse gating module and configured to:
        i. provide output stimulation pulses to the electrode contacts based on the gated electrode stimulation pulses, and
        ii. produce the gating feedback signal from the output stimulation pulses for the gating function.

11. The system according to claim 10, wherein the pulse gating module uses a leaky integrator gating function.

12. The system according to claim 10, wherein the pulse gating module uses a low pass filter gating function.

13. The system of claim 10, wherein the pulse gating module uses a gating function based on a mathematical model of stimulated tissue ion concentration.

14. The system of claim 10, wherein the pulse gating module uses a gating function based on a mathematical model of neurotransmitters in inner hair cells.

15. The system of claim 10, wherein the pulse gating module uses a gating function includes a frequency dependent weighting constant.

16. The system of claim 10, wherein the pulse gating module uses a gating function takes into account channel crosstalk between adjacent frequency channels.

17. The system of claim 10, wherein the pulse generation module produces stimulation pulses based on a continuous interleaved sampling (CIS) approach.

18. The system of claim 10, wherein the pulse generation module produces stimulation pulses based on a fine structure processing (FSP) approach.

* * * * *